United States Patent
Saito et al.

(10) Patent No.: US 8,379,792 B2
(45) Date of Patent: Feb. 19, 2013

(54) X-RAY CT APPARATUS

(75) Inventors: Yasuo Saito, Nasushiobara (JP); Miwa Okumura, Gifu (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 48 days.

(21) Appl. No.: 12/542,186

(22) Filed: Aug. 17, 2009

(65) Prior Publication Data

US 2010/0142670 A1    Jun. 10, 2010

(30) Foreign Application Priority Data

Aug. 20, 2008 (JP) ................................. 2008-211888

(51) Int. Cl.
*H05G 1/62* (2006.01)
*H05G 1/10* (2006.01)
*G01N 23/083* (2006.01)

(52) U.S. Cl. ............................. 378/8; 378/95; 600/428

(58) Field of Classification Search ................ 378/8, 95, 378/19; 600/428
See application file for complete search history.

(56) References Cited

U.S. PATENT DOCUMENTS

| | | | | |
|---|---|---|---|---|
| 6,298,260 B1 * | 10/2001 | Sontag et al. | ................. | 600/413 |
| 6,937,696 B1 * | 8/2005 | Mostafavi | ........................ | 378/95 |
| 7,050,537 B2 * | 5/2006 | Tsujii | ............................... | 378/95 |
| 7,177,386 B2 * | 2/2007 | Mostafavi et al. | ................ | 378/4 |
| 7,839,975 B2 * | 11/2010 | Nakamura et al. | .............. | 378/95 |
| 7,924,971 B2 * | 4/2011 | Knox et al. | ........................ | 378/8 |
| 8,041,001 B2 * | 10/2011 | Hirota et al. | ....................... | 378/8 |
| 2001/0049475 A1 * | 12/2001 | Bucholz et al. | ............... | 600/411 |
| 2004/0015073 A1 * | 1/2004 | Schell et al. | ................... | 600/411 |
| 2005/0119560 A1 * | 6/2005 | Mostafavi | ...................... | 600/425 |
| 2006/0074305 A1 * | 4/2006 | Mostafavi | ...................... | 600/428 |
| 2007/0286331 A1 * | 12/2007 | Keall et al. | ......................... | 378/8 |
| 2008/0056547 A1 * | 3/2008 | Kokubun et al. | ............... | 382/128 |
| 2008/0089463 A1 * | 4/2008 | Nakamura et al. | ................ | 378/4 |
| 2008/0123812 A1 * | 5/2008 | Sabol et al. | ...................... | 378/95 |

FOREIGN PATENT DOCUMENTS

| | | |
|---|---|---|
| JP | 5-42133 | 2/1993 |
| JP | 2001-242253 | 9/2001 |
| JP | 2003-245272 | 9/2003 |
| JP | 2005-40329 | 2/2005 |
| JP | 2007-275551 | 10/2007 |
| JP | 2008-136668 | 6/2008 |
| JP | 2008-246005 | 10/2008 |

OTHER PUBLICATIONS

Michael D. Silver, et al., "Volume CT of anthropomorphic phantoms using a radiation therapy simulator", SPIE Medical Imaging VI: Instrumentation, vol. 1651, 1992, pp. 197-211.

(Continued)

*Primary Examiner* — Thomas R Artman
(74) *Attorney, Agent, or Firm* — Oblon, Spivak, McClelland, Maier & Neustadt, L.L.P.

(57) ABSTRACT

According to the present invention, a subject is prompted to take breaths that are different at least in depth, and the subject's motion associated with respiration is captured. A timing when the subject is scanned is controlled according to the captured motion of the subject associated with respiration. A two-dimensional detector formed like a two-dimensional plane detects an X-ray beam having passed through the subject. Data is collected from the two-dimensional detector to acquire volume data on the subject.

12 Claims, 8 Drawing Sheets

OTHER PUBLICATIONS

Yasuo Saito, et al., "Large area 2-dimensional detector for real-time 3-dimensional CT (4D-CT)", SPIE Medical Imaging 2001: Physics of Medical Imaging, vol. 4320, 2001, pp. 775-782.

Notice of Reasons for Rejection mailed Nov. 6, 2012 in Japanese Patent Application No. 2008-211888 filed Aug. 20, 2008 (with English translation).

* cited by examiner

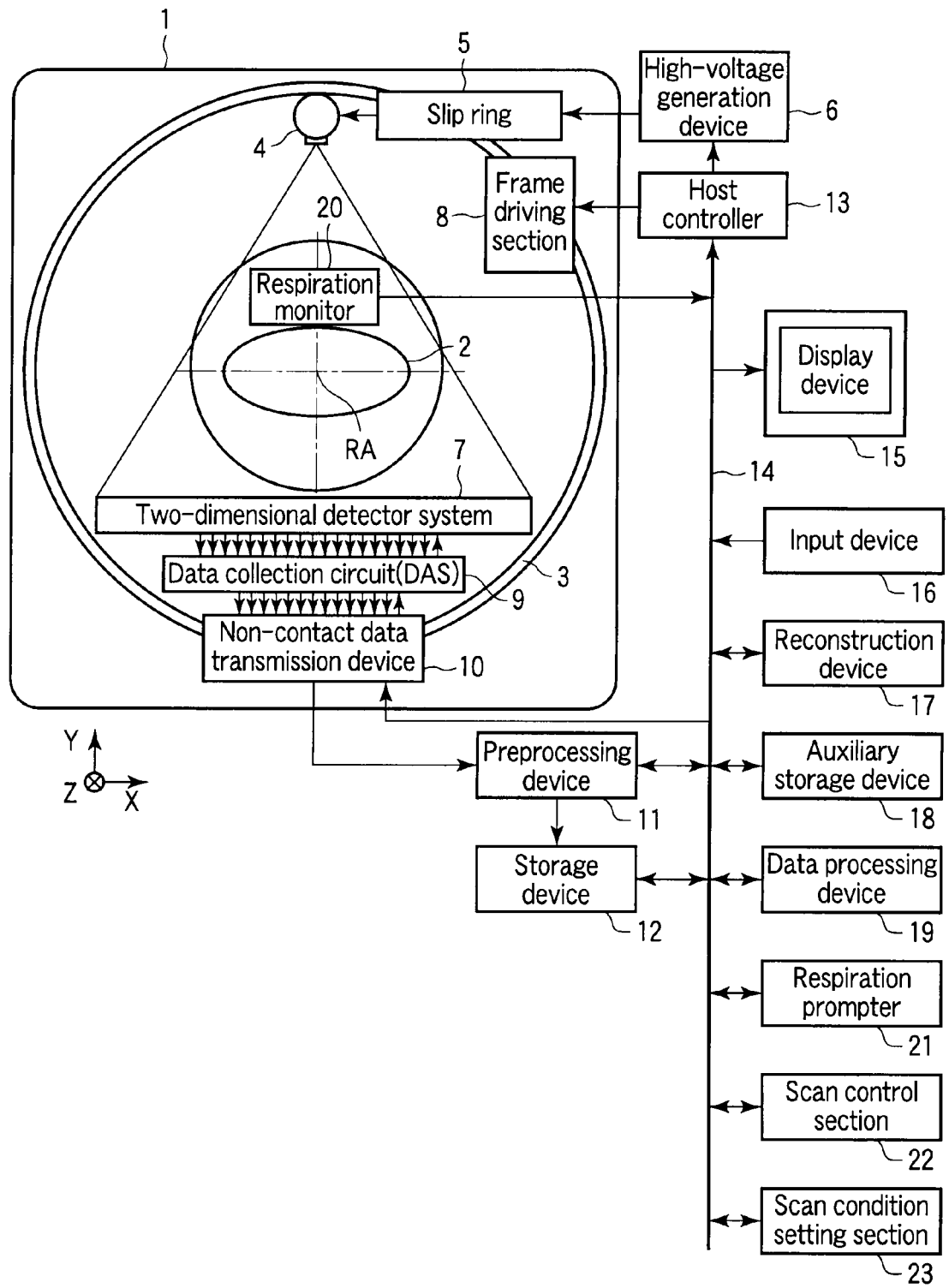
F I G. 1

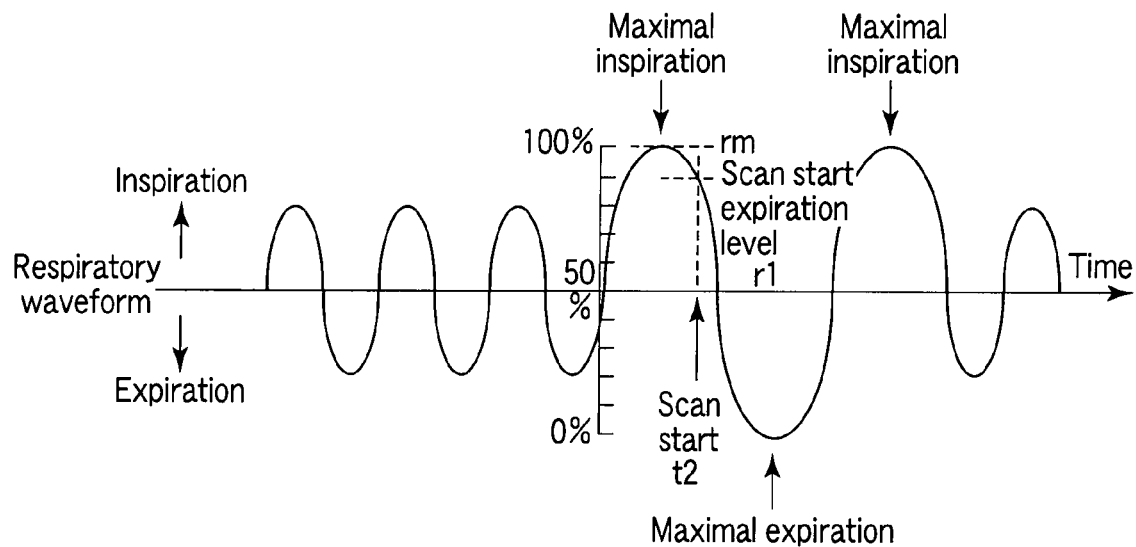
F I G. 4
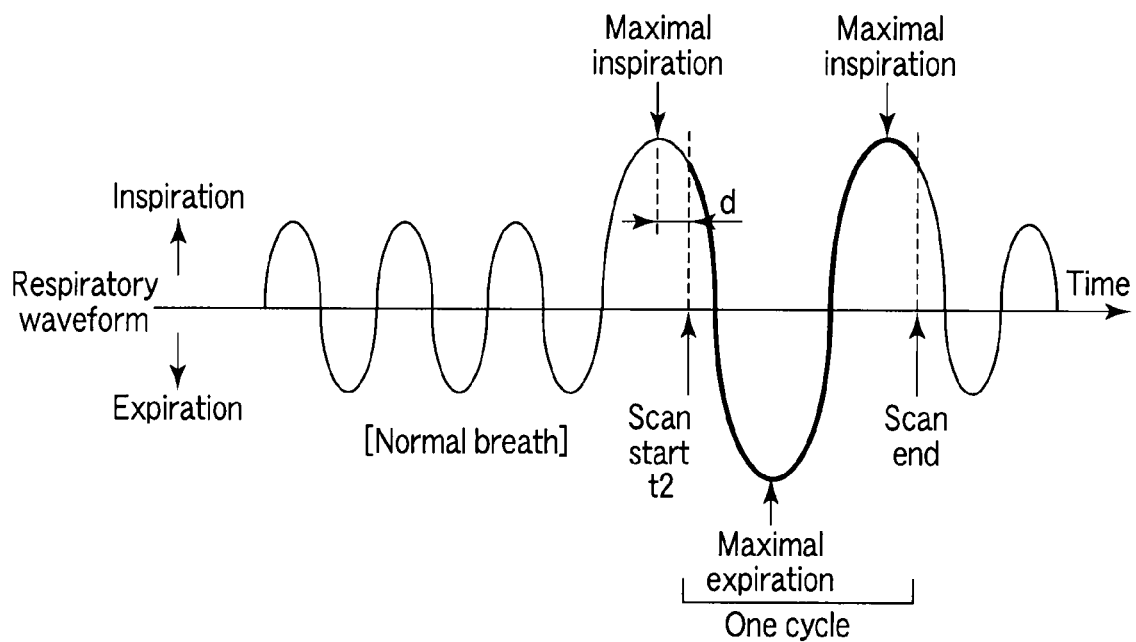
F I G. 5

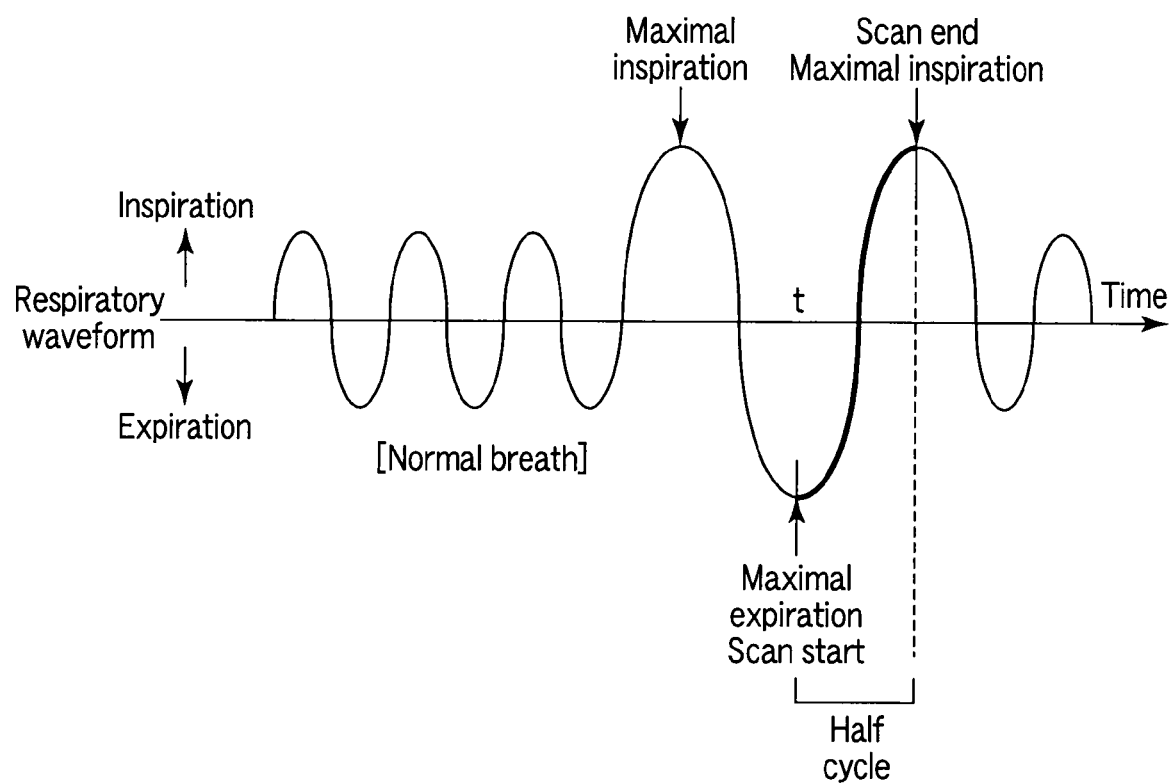
F I G. 6

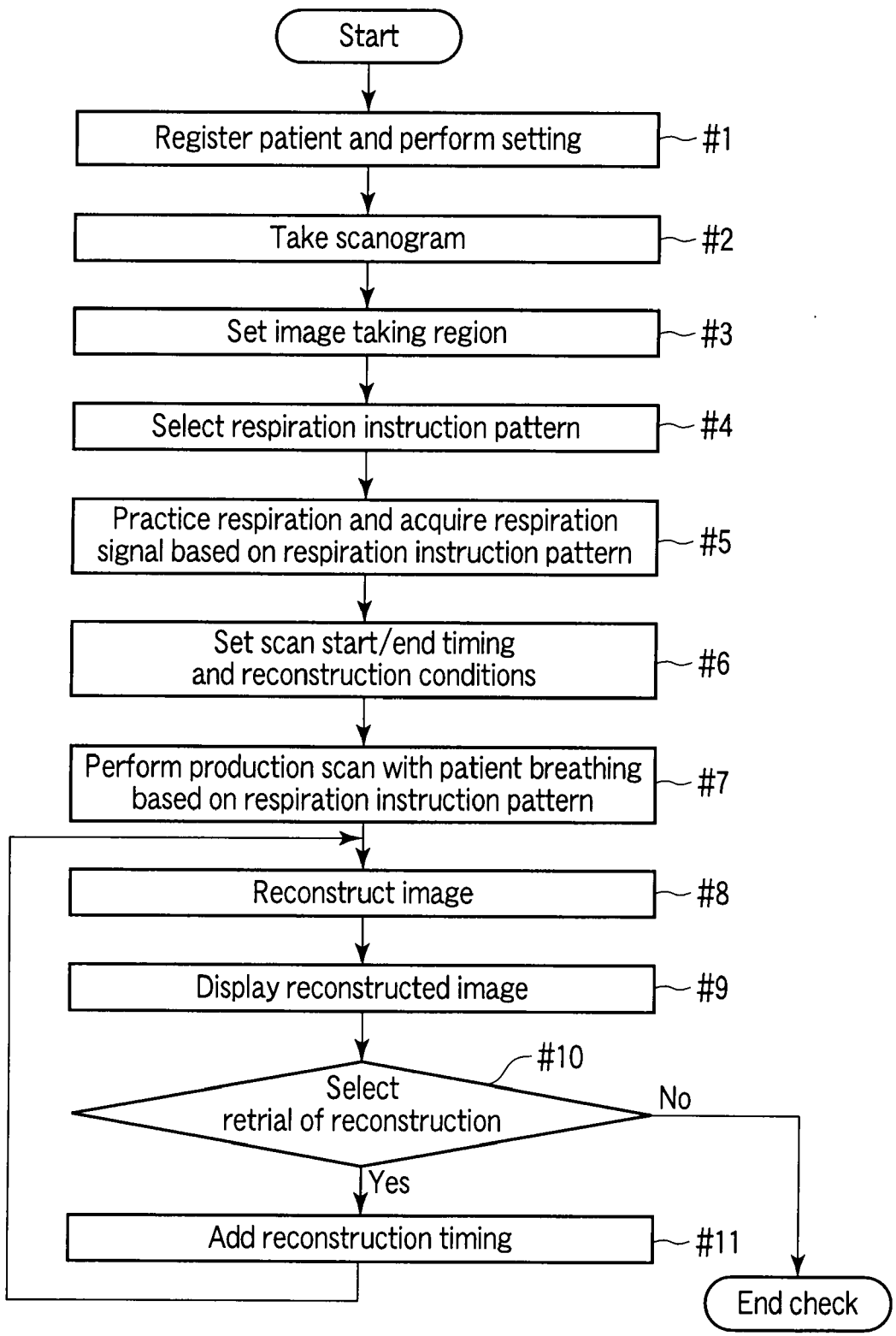
F I G. 7

X-RAY CT APPARATUS

CROSS-REFERENCE TO RELATED APPLICATIONS

This application is based upon and claims the benefit of priority from prior Japanese Patent Application No. 2008-211888, filed Aug. 20, 2008, the entire contents of which are incorporated herein by reference.

BACKGROUND OF THE INVENTION

1. Field of the Invention

The present invention relates to an X-ray computed tomography (CT) apparatus acquiring image data on a tomographic plane of a subject, for example, a patient, in synchronism with the subject's respiratory action, and in particular, to an X-ray CT apparatus including a two-dimensional detector detecting cone-beam X-rays emitted by an X-ray source and spreading in the direction of the subject's body axis (cone-beam [CT]).

2. Description of the Related Art

X-ray CT apparatuses are classified into, for example, fan beam (single slice) X-ray CT apparatuses, multi-slice X-ray CT apparatuses, and cone-beam X-ray CT scanners. Scan schemes for the X-ray CT apparatuses include, for example, helical scan and respiratory-gated scan (prospective-gating). Projection data acquired by helical scan is reconstructed by, for example, respiratory-gated reconstruction (retrospective-gating).

The fan beam X-ray CT operates as follows. The X-ray source emits fan-like X-ray beams. A plurality of detectors are arranged in a line in fan form so as to provide, for example, nearly 1,000 channels. The dose of X-rays having passed through a subject is detected by the plurality of detectors. The dose of X-rays detected by the plurality of detectors is digitally converted and collected by a data collection circuit. The data collection is performed about 1,000 times during one revolution of the X-ray source and the plurality of detectors revolved around the subject. Images are reconstructed based on the collected data.

The multi-slice X-ray CT includes an X-ray source emitting conical X-ray beams and a two-dimensional detector. The two-dimensional detector is made up of a plurality of detection elements arranged on a cylindrical plane so that N fan beam detection rows each of a plurality of (M) detection elements are stacked in the direction of a Z-axis (the direction of the subject's body axis). For the two-dimensional detector, the numbers of channels and segments are defined as M and N, respectively. The distance between the focus and the center of rotation and the diameter of an effective visual field are defined as FCD and FOV, respectively.

In the cone-beam X-ray CT scanner, the X-ray source emits wider X-ray beams in the direction of the subject's body axis. In the cone-beam X-ray CT scanner, data detected by the two-dimensional detector and collected from one direction corresponds to two-dimensional projection data. The cone-beam X-ray CT scanner performs three-dimensional image reconstruction based on two-dimensional projection data from multiple directions. The cone-beam X-ray CT scanner acquires voxel data on a certain volume simply by allowing the X-ray source and the two-dimensional detector to make one revolution.

For the cone-beam X-ray CT scanner, since the latter half of 1980s, research and development efforts has focused mainly on a system using an X-ray image intensifier as a two-dimensional detector. For example, the document "Volume CT of anthropomorphic phantoms using a radiation therapy simulator Michael D. Silver, Yasuo Saito, et al., SPIE 1651, 197-211, 1992" describes discussions on the results of scan of anthropomorphic phantoms using an experimental system that is a combination of a turntable and an image intensifier. The cone-beam X-ray CT scanner using the image intensifier has been used in some applications in order to capture the shape of an object offering a high contrast, for example, a bone or an imaged blood vessel.

A proposed cone-beam X-ray CT scanner includes scintillator similar to the multi-slice CT and photodiodes serving as detection elements. The proposed cone-beam X-ray CT scanner is combined with a continuously rotatable slip ring frame. The cone-beam X-ray CT scanner is described in, for example, the document "Large area 2-dimensional detector for real-time 3-dimensional CT (4D-CT), Yasuo Saito et al., SPIE 4320, 775-782, 2001".

An X-ray CT scanner using helical scan continuously revolves an X-ray tube and a detector around the subject, while moving a bed top plate with the subjected lying thereon, in the direction of the subject's body axis. Thus, the X-ray tube follows a spiral track relative to the subject.

To reconstruct an image, the X-ray CT scanner performs scan at a timing for a preset phase of respiratory movement obtained using a device monitoring the subject's respiratory action to collect data corresponding to a certain portion of the track of the X-ray tube. The monitoring device monitoring the subject's respiratory action may be, for example, a pressure sensor attached to the subject's chest, an air flow sensor measuring the flow rate of the subject's breath, or a device determining the respiratory movement by allowing software to analyze the subject's motion the image of which is captured by a camera.

The X-ray CT scanner uses a 360° interpolation method or a 180° interpolation method. The 360° interpolation method uses data for 180° on the opposite sides of a slice plane. The 180° interpolation method uses data for a total of 180° across the slice plane which is obtained using opposite beams.

The respiratory-gated scan adjusts scan timings in synchronism with the subject's breath during the scan. The monitoring device monitors the subject's respiratory action. The monitoring device may be, for example, a pressure sensor attached to the subject's chest, an air flow sensor measuring the flow rate of the subject's breath, or a device determining the respiratory movement by allowing software to analyze the subject's motion the image of which is captured by a camera, as described above. The respiratory-gated scan is performed at a timing for a preset phase of the subject's respiratory movement monitored by the monitoring device.

A technique is available for acquiring images of the same respiratory phase over a broad range in the direction of the subject's body axis. The technique repeats performing a scan in which the X-ray tube and the detector make one revolution around the subject at rest and moving the subject.

Specifically, first, the subject is moved in order to allow an image of a required slice position of the subject to be acquired. In this condition, the scan is performed at a timing for a preset respiratory phase. Then, the subject is moved in order to allow an image of the next required position of the subject to be acquired. The subject waits for the scan to be performed at the timing for the preset respiratory phase. If such a scan is performed to acquire volume data at different respiratory phases, the above-described series of operations are repeated at different respiratory phases.

In the respiratory-gated reconstruction, a postprocess is executed in which projection data acquired by the helical scan and which is consecutive in the directions of time and the subject's body axis is reconstructed into volume data for any respiratory phase. The monitoring device monitoring the subject's respiratory action may be, for example, a pressure sensor attached to the subject's chest, an air flow sensor measuring the flow rate of the subject's breath, or a device determining the respiratory action by allowing software to analyze the subject's motion the image of which is captured by a camera, as described above. The monitoring device monitoring the subject's respiratory action monitors the subject's respiratory action to output respiratory monitoring signals, for example, gate pulses or waveforms.

To perform the respiratory-gated reconstruction, the respiratory monitoring signals output by the monitoring device are stored together with the projection data. In the respiratory-gated reconstruction, data required to reconstruct the respiratory phase specified based on the respiratory monitoring signal is extracted from the projection data, to reconstruct an image covering the specified range. To allow an image for any position and any respiratory phase to be reconstructed, data on the same slice position needs to be collected for one cycle of respiratory time interval. Thus, the range of helical pitch is limited by the respiratory cycle, the number of detector rows, and the like.

However, one respiratory-gate scan allows volume data to be obtained for only one particular type of respiratory phase. Thus, images involving the subject's motion associated with the respiratory movement cannot be observed. By repeating the scan with the specified respiratory phase varied, volume data can be obtained for some respiratory phases. However, this is still insufficient for observing the subject's consecutive motions associated with the respiratory movement.

The respiratory-gated reconstruction enables the subject's motion to be observed under the precondition that the same breath is repeated. However, because of the precondition that the same breath is repeated, the respiratory-gated reconstruction is limited to resting respiration. Thus, the respiratory-gated reconstruction fails to enable diagnostic functional analysis based on motion associated with a conscious deep breath, for example, the motion between the maximal expiration and the maximal inspiration. For example, during the subject's maximal expiration or maximal inspiration, images of a site that cannot be observed at a resting respiratory level, for example, images of a tumor site, can be observed.

However, the respiratory-gated reconstruction is limited to the resting respiration, and thus has difficulty acquiring images during, for example, the subject's maximal expiration or maximal inspiration.

Such a cone-beam X-ray CT scanner is described in, for example, Jpn. Pat. Appln. KOKAI Publication No. 2001-242253.

An object of the present invention is to provide an X-ray CT apparatus allowing volume data to be obtained for any respiratory phase of the subject's motion associated with deep respiratory movement, even during a non-reproducible breath such as a conscious deep breath.

BRIEF SUMMARY OF THE INVENTION

An X-ray CT apparatus according to a first aspect of the present invention comprises an X-ray generation section irradiating a subject with a cone-beam X-ray emitted by an X-ray source, a two-dimensional detector formed like a two-dimensional plane to detect the X-ray beam having passed through the subject, a data acquisition section collecting data from the two-dimensional detector to acquire volume data on the subject, a respiration prompter prompting the subject to take breaths that are different at least in depth, a respiration monitor capturing the subject's motion associated with respiration, and a scan control section controlling timing for irradiation of the subject with the X-ray beam according to the subject's motion associated with respiration and captured by the respiration monitor.

A scan control method for an X-ray CT apparatus according to a second aspect of the present invention comprises allowing a respiration prompter to prompt a subject to take breaths that are different at least in depth, allowing a respiration monitor, when the subject is prompted by the respiration prompter to take breaths that are different at least in depth, to capture the subject's motion associated with respiration, allowing a scan control section to control a timing when the subject is irradiated with a cone-beam X-ray emitted by an X-ray source, according to the subject's motion associated with respiration and captured by the respiration monitor, allowing a two-dimensional detector formed like a two-dimensional plane to detect the X-ray beam having passed through the subject, and allowing a data acquisition section to collect data from the two-dimensional detector to acquire volume data on the subject.

BRIEF DESCRIPTION OF THE SEVERAL VIEWS OF THE DRAWING

FIG. 1 is a diagram showing the configuration of a first embodiment of a cone-beam X-ray CT apparatus according to the present invention;

FIG. 4 is a diagram showing an example of a method of specifying the depth of a breath as a scan start timing for the subject in the apparatus shown in FIG. 1;

FIG. 5 is a diagram showing that the apparatus starts a scan at a certain respiratory phase of the subject and ends the scan at the same respiratory phase one cycle later;

FIG. 6 is a diagram showing that the apparatus starts a scan at the subject's maximal expiration and ends the scan at the subject's maximal inspiration, that is, a half cycle of respiratory phase later;

FIG. 7 is a flowchart of the operation of the apparatus during a continuous dynamic scan;

DETAILED DESCRIPTION OF THE INVENTION

Figure 2:
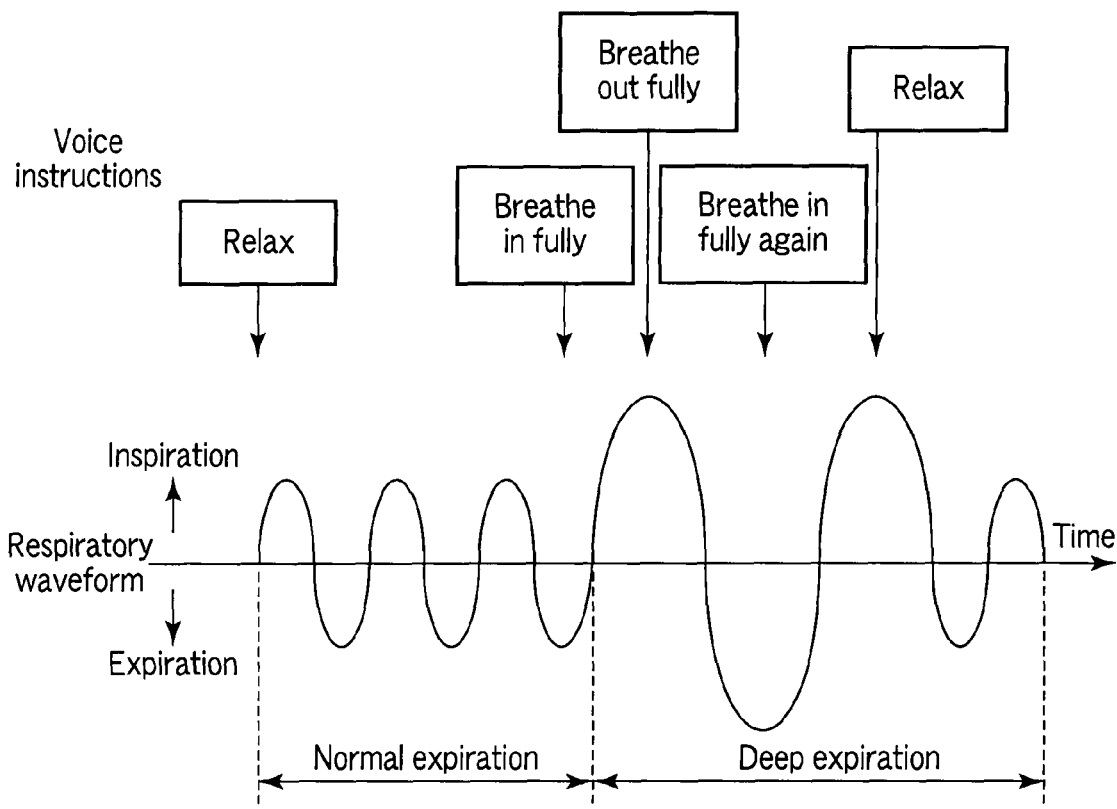
FIG. 2 is a diagram showing examples of voice instructions for respiration and the respiratory waveform of a subject monitored by a respiration monitor in the apparatus shown in FIG. 1.

A first embodiment of the present invention will be described below with reference to the drawings.

FIG. 1 is a diagram showing the configuration of a cone-beam X-ray CT apparatus. The cone-beam X-ray CT apparatus includes a gantry 1. The gantry 1 has a bed on which a subject 2 is laid. The gantry 1 includes a ring-like rotating frame 3 held so as to be rotatable around a center-of-rotation axis RA. An X-ray tube 4 is attached to the rotating frame 3 opposite the center-of-rotation axis RA. A high-voltage generation device 6 is connected to the X-ray tube 4 via a slip ring 5. The high-voltage generation device 6 applies a high voltage to the X-ray tube 4 via the slip ring 5. When the high voltage is applied to the X-ray tube 4, the X-ray tube 4 emits cone-beam X-rays (cone-beams). The X-ray tube 4 forms an X-ray generation section.

A two-dimensional detector system 7 is attached onto the rotating frame 3. The two-dimensional detector system 7 is formed like a two-dimensional plane. The two-dimensional detector system 7 detects X-ray beams emitted by the X-ray tube 4 and transmitted through the subject 2. The two-dimensional detector system 7 lies opposite the X-ray tube 4 across the center-of-rotation axis RA. The two-dimensional detector system 7 is specified for multiple slices. The two-dimensional detector system 7 has many rows of detection elements provided along a direction parallel to the center-of-rotation axis RA, that is, along the direction of the body axis (slice direction). The two-dimensional detector system 7 has a wide detection range in the direction of the subject's body axis (Z-axis direction). The many rows of detection elements are composed of, for example, scintillators and photo diodes. The number of the detection element rows is, for example, 64. Each of the detection element rows has a plurality of detection elements arranged along a channel direction.

The center-of-rotation axis RA is defined as a Z-axis. An XY coordinate system is used to define a rotation coordinate system around the Z-axis. In this case, a what is called an X-ray center axis connecting the focus of the X-ray tube 4 to the center of the two-dimensional detection system 7 is defined as a Y-axis. An axis orthogonal to the Z- and Y axes is defined as an X-axis. The X-, Y-, and Z-axes will be appropriately referenced below.

A data collection circuit 9 is connected to the two-dimensional detection system 7. The data collection circuit 9 is generally called a data acquisition system (DAS). The DAS 9 converts an output (current signal) from each channel of the two-dimensional detection system 7 into a voltage signal, and amplifies and converts the voltage signal into a digital signal. A preprocessing device 11 is connected to the DAS 9 via a non-contact transmission device 10 using light or magnetism as a medium. The preprocessing device 11 corrects, for example, the inter-channel non-uniformity of the output from the DAS 9 and outputs resulting projection data. The projection data output by the preprocessing device 11 is stored in a storage device 12.

A host controller 13 connects to the high-voltage generation device 6, a frame driving section 8, the preprocessing section 11, the storage device 12, a display device 15, an input device 16, a reconstruction device 17, an auxiliary storage device 18, a data processing device 19, a respiration monitor 20, a respiration prompter 21, a scan control section 22, and a scan condition setting section 23 via a data/control bus 14.

The host controller 13 controls the high-voltage generation device 6, the frame driving section 8, the preprocessing section 11, the storage device 12, the display device 15, the input device 16, the reconstruction device 17, the auxiliary storage device 18, the data processing device 19, the respiration monitor 20, the respiration prompter 21, the scan control section 22, and the scan condition setting section 23 via the data/control bus 14.

The host controller 13 rotates the rotating frame 3 to move revolvingly. Concurrently, the host controller 13 controls the high-voltage generation device 6 and the DAS 9 to perform, for example, a prescan (dynamic scan) or a production scan (dynamic scan). The prescan is also referred to as a monitoring scan.

The input device 16 is a pointing device such as a mouse, a keyboard, and the like and is manually operated by an operator.

For example, during the prescan or production scan, the reconstruction device 17 reconstructs CT images of the subject 2, for example, 3D image (three-dimensional image) data or 4D image data, from the projection data preprocessed by the preprocessing device 11.

The storage device 12 stores, for example, the projection data preprocessed by the preprocessing device 11, 3D image data, sectional image data relating to three-orientation cross sections, for example, an axial cross section, a coronal cross section, and a sagittal cross section and obtained by multi-processor reconstruction (MPR), image data such as maximum intensity projection (MIP) images, and 4D imaging CT image data acquired during the prescan or production scan.

The data processing device 19 carries out image processing, for example, generation, from 3D image data, of sectional image data relating to three-orientation cross sections, for example, an axial cross section, a coronal cross section, and a sagittal cross section and obtained by multiprocessor reconstruction (MPR), and generation of MIP images from 3D image data.

The respiration monitor 20 captures the subject's motion associated with respiration to output a respiration monitoring signal. The respiration monitor 20 may be, for example, a pressure sensor attached to the chest of the subject 2, an air flow sensor measuring the flow rate of the breath of the subject 2, or a device determining the respiratory movement by allowing software to analyze the motion of the subject 2 the image of which is captured by a camera.

The respiration prompter 21 prompts the subject 2 to take breaths with different depths. The respiration prompter 21 acoustically prompts the subject to take conscious breaths with different depths, for example, a normal breath (resting breath) and a deep breath. Specifically, before and during the scan, the respiration prompter 21 outputs, for example, the voice messages "Relax", "Breathe in fully", "Breathe out fully", "Breathe in fully again", and "Relax" to prompt the subject 2 to take breaths with different depths.

FIG. 2 shows an example of the relationship between voice instructions for respiration and the respiratory waveform of the subject 2 monitored by the respiration monitor 20. The upper half of FIG. 2 shows voice instructions prompting the subject 2 to take a breath. The lower half of FIG. 2 shows the respiratory waveform of the subject 2 corresponding to the voice instructions. For the respiratory waveform of the subject 2, the axis of abscissa indicates time, and the axis of ordinate indicates a respiration level, that is, the depth of the breath. The respiratory waveform of the subject 2 monitored by the respiration monitor 20 is displayed, for example, on the display device 15.

An example of a pattern of instructions on the breath of the subject 2 will be described. The respiration prompter 21 first outputs the voice message "Relax". Thus, the subject 2 maintains a normal breath (resting breath).

Then, the respiration prompter 21 outputs the voice message "Breathe in fully". Thus, the subject 2 takes a deep breath to enter a maximal inspiration state.

Then, the respiration prompter 21 outputs the voice message "Breathe out fully". Thus, the subject 2 breathes out fully to enter a maximal expiration state.

Then, the respiration prompter 21 outputs the voice message "Breathe in fully again". Thus, the subject 2 takes a deep breath again to enter the maximal inspiration state again.

Then, the respiration prompter 21 outputs the voice message "Relax". Thus, the subject 2 returns to the normal breath (resting breath).

The voice instructions "Relax", "Breathe in fully", "Breathe out fully", "Breathe in fully again", "Relax", and the like may be preset in the respiration prompter 21 so that the respiration prompter 21 can automatically generate the voice instructions. Alternatively, the operator performs manual operation to sequentially generate the voice instructions while observing the respiratory waveform of the subject 2 monitored by the respiration monitor 20 and displayed on the display device 15.

A plurality of respiration instruction patterns for the subject 2 may be registered in the respiration prompter 21 so that the operator can select, for example, one of the plurality of respiration instruction patterns.

The scan control section 22 controls timings for scans of the subject 2 according to the motion of the subject 2 associated with respiration captured by the respiration monitor 20. That is, the scan control section 22 controls timings for irradiation of the subject with X-ray beams according to the motion of the subject 2 associated with respiration and captured by the respiration monitor 20. The scan control section 22 controls timings for the start and end of each scan (irradiation with X-ray beams) according to the respiratory phase or level of the subject 2. For example, two methods are available for the start timing for the scan (irradiation with X-ray beams) of the subject 2. A first method specifies the respiratory phase of the subject 2 as an indication of the elapse of time. A second method specifies the respiratory level of the subject 2 as an indication of the depth of the breath.

Figure 3:
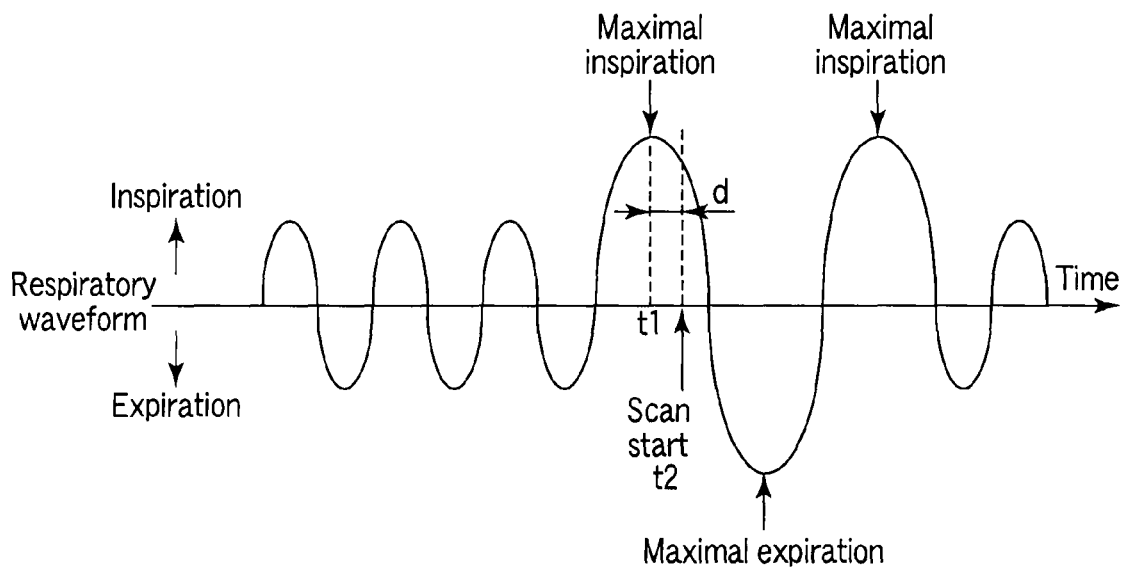
FIG. 3 is a diagram showing an example of a method of specifying the subject's respiratory phase as a scan start timing for the subject in the apparatus shown in FIG. 1.

FIG. 3 shows an example of the method of specifying the respiratory phase of the subject 2 as a scan start timing for the subject 2. The scan control section 22 starts a scan at time t2, that is, a predetermined delay time (d) after time t2 corresponding to the maximal inspiration based on the respiratory phase of the subject 2 captured by the respiration monitor 20. Here, the scan start time is set based on the respiratory phase of the maximal inspiration.

The setting for the scan start is not limited to this aspect. The scan start time may be set based on the respiratory phase of the maximal expiration. An absolute time may be set for the delay time (d). With the time interval between the maximal inspiration and the maximal expiration defined as, for example, 100%, the delay time (d) may be set to correspond to a point in time that is, for example, 10% of the time interval after the time of the maximal inspiration.

FIG. 4 shows an example of the method of specifying the depth of a breath as a scan start timing for the subject 2. The scan control section 22 starts a scan at time t10 corresponding to an inspiration level r1 indicating a predetermined percentage, for example, 10% lower than an inspiration level rm indicative of the maximal inspiration based on the respiratory phase of the subject 2 captured by the respiration monitor 20. In this case, the maximal inspiration is defined as 100%, and the maximal expiration is defined as 0%. Alternatively, the maximal inspiration may be defined as +100%, the maximal expiration may be defined as −100%, If the scan start timing is set based on the depth of a breath, the respiratory waveform of the subject 2 passes through the same inspiration level plural times. Thus, the scan start timing may be set based on a combination of the respiratory phase of the subject 2 and the depth of the breath. For example, the scan start timing may be set to be the first point in time when the expiration level becomes lower than 90%, after the peak of the expiration following an instruction for a deep breath.

On the other hand, for the timing for ending the scan of the subject 2, the following three methods are available: a first method of specifying the respiratory phase of the subject 2 and a second method of specifying the respiratory level of the subject, as is the case with the scan start, and a third method of specifying a respiratory cycle for collection of projection data.

FIGS. 5 and 6 show examples of the method of specifying the scan end timing based on the respiratory cycle. FIG. 5 shows that a scan is started at a certain respiratory phase of the subject and ended at the same respiratory phase one cycle later. FIG. 6 shows that collection of projection data is started at the maximal expiration of the subject 2 and ended at the maximal inspiration of the subject 2, that is a half cycle (0.5 cycle) of respiratory phase later. The scan control section 22 ends a scan one cycle or a half cycle of respiratory phase after the start of the scan.

If projection data needs to be collected both during the inspiration of the subject 2 and during the expiration of the subject 2, the collection needs to be continued for at least one cycle of respiratory phase. In this case, the shortest scan time corresponds to the method of starting a scan at a certain respiratory phase of the subject 2 and ended at the same respiratory phase one cycle later.

If projection data needs to be collected either during the inspiration of the subject 2 or during the expiration of the subject 2, the shortest scan time corresponds to the half cycle between peaks of the respiratory phase, that is, from maximal inspiration to maximal expiration or from maximal expiration to maximal inspiration.

The scan condition setting section 23 sets the start and end of a scan according to the respiratory phase or level of the subject 2, based on the respiratory waveform of the subject 2 displayed on the display device 15. The scan condition setting section 23 sets the scan start timing as described above.

The scan condition setting section 23 sets the scan start timing to be time t2 that is the predetermined delay time (d) after time t1 corresponding to the maximal expiration, based on the respiratory phase of the subject 2 captured by the respiration monitor 20, as shown in FIG. 3.

The scan condition setting section 23 sets the scan start timing to be time t10 corresponding to the inspiration level r1 that is a predetermined percentage, for example, 10% lower than the inspiration level rm indicating the maximal inspiration, based on the respiratory phase of the subject 2 captured by the respiration monitor 20 as shown in FIG. 4.

The scan condition setting section 23 sets the scan end timing as described above. As shown in FIG. 5, the scan condition setting section 23 sets the scan end timing to be the same respiration phase one cycle later.

As shown in FIG. 6, the scan condition setting section 23 sets the scan end timing to be the respiratory phase corresponding to the maximal inspiration that is a half cycle of respiratory phase after the maximal expiration.

The scan condition setting section 23 may automatically set the start and end of the scan based on the respiratory waveform of the subject 2. Alternatively, the scan condition setting section 23 may be set by the operator by performing manual operation while observing the respiratory waveform of the subject 2 displayed on the display device 15.

Now, the operation of the apparatus configured as described above will be described with reference to the operation flowchart shown in FIG. 7. Here, the dynamic scan will be described by way of example.

In step #1, the subject 2 such as a patient is registered, and the present apparatus is set. The subject 2 is laid on a bed in the gantry 1.

Then, in step #2, before acquiring a CT image of the subject 2, the present apparatus acquires a two-dimensional scan image of the subject 2. The scan image is acquired in order to determine, for example, the start position of the present scan and image capture conditions for acquiring the CT image.

The scan image of the subject 2 is acquired as follows. The position of the X-ray tube 4 is fixed to a predetermined angle of rotation. The bed is moved in the Z-direction. At this time, the X-ray tube 4 irradiates the subject 2 with X-ray beams. The two-dimensional detector system 7 receives the X-ray beams having passed through the subject 2. The two-dimensional detector system 7 outputs an X-ray beam detection signal corresponding to the quality of X-ray beams received, to each light receiving element.

The DAS 9 converts the X-ray beam detection signal output to each light receiving element by the two-dimensional detection system 7, into a voltage signal, amplifies the voltage signal, and further converts the amplified signal into a digital signal.

The preprocessing device 11 corrects the inter-channel non-uniformity and the like of outputs from the DAS 9 and outputs the resulting projection data. The projection data output by the preprocessing device 11 is stored in the storage device 12.

The host controller 13 allows, for example, a scan image acquisition section to operate to acquire scan images of the subject 2 from the digital X-ray beams from the DAS 9.

The two-dimensional scan images of the subject 2 are displayed on the display device 15 by the host controller 13. The operator observes the two-dimensional scan images of the subject 2 displayed on the display device 15. Then, the operator, for example, manually operates the input device 16 to input the image capture range. The operator, for example, manually operates the input device 16 to select a respiration instruction pattern for the subject 2.

In step #3, the host controller 13 sets the image capture range for the subject 2. In the next step #4, the host controller 13 sets the respiration instruction pattern for the subject 2. Thus, the respiration prompter 21 selects, for example, one of the plurality of respiration instruction patterns pre-registered.

Then, before the actual production scan, the subject 2 practices conscious breathes through voice instructions.

In step #5, the respiration prompter 21 outputs the voice message "Relax". Thus, the subject 2 maintains the normal breath (resting breath).

Then, the respiration prompter 21 outputs the voice message "Breathe in fully". Thus, the subject 2 takes a deep breath to enter the maximal inspiration state.

Then, the respiration prompter 21 outputs the voice message "Breathe out fully". Thus, the subject 2 breathes out fully to enter the maximal expiration state.

Then, the respiration prompter 21 outputs the voice message "Breathe in fully again". Thus, the subject 2 takes a deep breath again to enter the maximal inspiration state again.

Then, the respiration prompter 21 outputs the voice message "Relax". Thus, the subject 2 returns to the normal breath (resting breath).

Concurrently, in step #5, the respiration monitor 20 captures the motion of the subject 2 associated with respiration when the subject takes a breath in response to the voice instructions for respiration output by the respiration prompter 21. The respiration monitor 20 then outputs the resulting respiration monitoring signal. The respiration monitoring signal output by the respiration monitor 20 is stored in, for example, storage device 12. Concurrently, the respiration monitoring signal output by the respiration monitor 20 is transmitted to the display device 15, which displays a respiratory waveform, for example, as shown in FIG. 2.

Then, in step #6, the scan condition setting section 23 sets the start and end of the production scan according to the respiratory phase or level of the subject 2, based on the respiratory waveform of the subject 2 displayed on the display device 15.

Specifically, as described above, the scan condition setting section 23 sets the start timing for the production scan to be time t2 that is the predetermined delay time (d) after time t1 corresponding to the maximal expiration, based on the respiratory phase of the subject 2 captured by the respiration monitor 20 as shown in FIG. 3.

Alternatively, as described above, the scan condition setting section 23 sets the start timing for the production scan to be time t10 corresponding to the inspiration level r1 that is a predetermined percentage, for example, 10% lower than the inspiration level rm indicating the maximal inspiration, based on the respiratory phase of the subject 2 captured by the respiration monitor 20 as shown in FIG. 4.

The scan condition setting section 23 sets the production scan end timing as described above. As shown in FIG. 5, the scan condition setting section 23 sets the production scan end timing to be the same respiration phase of the subject 2 one cycle later.

Alternatively, as described above, the scan condition setting section 23 sets the production scan end timing to be the respiratory phase of the subject 2 corresponding to the maximal inspiration that is a half cycle of respiratory phase after the maximal expiration.

The scan condition setting section 23 may automatically set the start and end of the production scan. The start and end of the production scan may be set by the operator by performing manual operation while observing the respiratory waveform of the subject 2 displayed on the display device 15. Alternatively, a plurality of different timings may be set for each of the start and end of the production scan.

The scan control section 22 controls the timings for the production scan in response to the motion of the subject 2 associated with respiration, according to the start and end timings for the production scan set by the scan condition setting section 23. The reconstruction device 17 is set to reconstruct the volume data on the subject 2 acquired by timing control by the scan control section 22, to acquire a three-dimensional image of the desired respiratory phase.

Then, in step #7, the host controller 13 instructs the respiration prompter 21 to provide the subject 2 with the voice instructions of the same respiration instruction pattern as that for the practice of conscious breaths. The host computer 13 allows the display device 15 to display respiration monitoring signals output by the respiration monitor 20.

During the production scan, the respiration prompter 21 first outputs the voice message "Relax". Thus, the subject 2 maintains the normal breath (resting breath).

Then, the respiration prompter 21 outputs the voice message "Breathe in fully". Thus, the subject 2 takes a deep breath to enter the maximal inspiration state.

Then, the respiration prompter 21 outputs the voice message "Breathe out fully". Thus, the subject 2 breathes out fully to enter the maximal expiration state.

Then, the respiration prompter 21 outputs the voice message "Breathe in fully again". Thus, the subject 2 takes a deep breath again to enter the maximal inspiration state again.

Then, the respiration prompter 21 outputs the voice message "Relax". Thus, the subject 2 returns to the normal breath (resting breath).

Concurrently, the respiration monitor 20 captures the motion of the subject 2 associated with respiration when the subject takes a breath in response to the voice instructions for respiration output by the respiration prompter 21. The respiration monitor 20 then outputs the resulting respiration monitoring signal. The respiration monitoring signal output by the respiration monitor 20 is stored in, for example, storage device 12. Concurrently, the respiration monitoring signal output by the respiration monitor 20 is transmitted to the display device 15, which displays a respiratory waveform, for example, as shown in FIG. 2.

In step #7, the host computer 13 outputs an instruction to perform the production scan, to the high-voltage generation device 6, the frame driving section 8, and the like via the data/control bus 14 so that the production scan is started at time t2 that is the predetermined delay time (d) after time t1 corresponding to the maximal expiration, based on the respiratory phase of the subject 2 captured by the respiration monitor 20, for example, as shown in FIG. 3.

Alternatively, also in step #7, the host computer 13 outputs an instruction to perform the production scan, to the high-voltage generation device 6, the frame driving section 8, and the like via the data/control bus 14 so that the production scan is started at time t10 corresponding to the inspiration level r1 that is a predetermined percentage, for example, 10% lower than the inspiration level rm indicating the maximal inspiration, based on the respiratory phase of the subject 2 captured by the respiration monitor 20, for example, as shown in FIG. 4.

With the subject 2 taking a conscious breath according to the voice instructions of the respiration instruction pattern, the X-ray tube 4 and the two-dimensional detection system 7 starts revolving continuously substantially around the subject 2, for example, at time t2 shown in FIG. 3 or time t10 shown in FIG. 4.

During the production scan, X-ray beams emitted by the X-ray tube 4 pass through the subject 2 and are then detected by the two-dimensional detection system 7. As described above, the DAS 9 converts an output through each channel of the two-dimensional detection system 7, into a voltage signal, amplifies the voltage signal, and further converts the amplified signal into a digital signal. The preprocessing device 11 corrects the inter-channel non-uniformity and the like of outputs from the DAS 9 and outputs the resulting projection data. The projection data preprocessed by the preprocessing device 11 is stored in the storage device 12.

When the production scan starts at a certain respiratory phase of the subject 2 and reaches the same respiratory phase one cycle later, for example, as shown in FIG. 5, the host computer 13 outputs an instruction to end the production scan, to the high-voltage generation device 6, the frame driving section 8, and the like via the data/control bus 14 so as to end the production scan.

Alternatively, when the production scan starts at the maximal expiration of the subject 2 and reaches the maximal inspiration a half cycle of respiratory phase later as shown in FIG. 6, the host computer 13 outputs an instruction to end the production scan, to the high-voltage generation device 6, the frame driving section 8, and the like via the data/control bus 14 so as to end the production scan.

Then, in step #8, for example, during the production scan, the reconstruction device 17 reconstructs CT images of the subject 2, for example, 3D image data or 4D image data, from the projection data preprocessed by the preprocessing device 11. In this case, the reconstruction device 17 operates according to the production scan start and end timings set by the scan condition setting section 23. For example, as shown in FIG. 5, the production scan starts at time t2 that is the predetermined delay time (d) after time t1 corresponding to the maximal expiration, and the reconstruction section 17 reconstructs projection data collected until one cycle of respiratory cycle after the scan start time t2, that is, until the subject 2 reaches the same respiratory phase as that at time 2. Thus, a three-dimensional image of the desired respiratory phase is acquired.

Then, in step #9, the host computer 13 displays, on the display device 15, the three-dimensional image of the subject 2 at the desired respiratory phase acquired by the reconstruction device 17.

Then, in step #10, the host computer 13 determines whether or the reconstruction is selected to be retried. If the host computer 13 determines that the reconstruction is selected to be retried, the host computer 13 shifts to step #11 to add a timing for image reconstruction.

Then, the host computer 13 returns to step #8 to allow the reconstruction device 17 to reconstruct the image again. If the reconfiguration is not selected to be retried, the host computer 13 ends the check.

Thus, according to the above-described first embodiment, the respiration prompter 21 outputs, for example, the voice messages "Relax", "Breathe in fully", "Breathe out fully", "Breathe in fully again", and "Relax", to the subject 2 to prompt the subject 2 to take conscious breathes with different depths. At this time, the X-ray tube 4 and the two-dimensional detection system 7 are continuously moved revolvingly substantially around the subject 2 to perform a continuous dynamic scan. Thus, projection data is collected.

Projection data can be collected not only while the subject 2 is breathing at rest but also when the subject 2 takes, for example, a breath ranging from the maximal expiration to the maximal inspiration. The reconstruction of the projection data, for example, enables a site that is hidden behind another site and cannot be observed at the resting respiration level, for example, a tumor site, to appear during the maximal expiration or the maximal inspiration. Thus, a CT image of the site can be observed.

Thus, diagnostic functional analysis or the like is enabled which is based on the motion of the subject 2 associated with a conscious deep breath, for example, the motion between the maximal expiration and the maximal inspiration. Consequently, even for a non-reproducible breath, projection data can be collected at any respiratory phase. Then, a CT image can be acquired by reconstructing the projection data.

Now, a second embodiment of the present invention will be described with reference to the drawings. In the present embodiment, the configuration of the cone-beam X-ray CT apparatus in the present embodiment is the same as that shown in FIG. 1 and will not be described in detail.

In the description of the present embodiment, the cone-beam X-ray CT apparatus repeats a single scan. In the continuous dynamic scan according to the above-described first embodiment, if the subject 2 has a low respiration rate and a CT image need not be captured for a large number of respiratory phases, then more production scans than required are performed. Then, the subject 2 is exposed to an excessively large amount of X-ray beams.

Thus, in the description of the present embodiment, the cone-beam X-ray CT apparatus repeats a single scan with the respiratory phase varied.

In the present embodiment, as is the case with the first embodiment, before and during the scan, the respiration prompter 21 outputs, for example, the voice messages "Relax", "Breathe in fully", "Breathe out fully", "Breathe in fully again", and "Relax" to prompt the subject 2 to take breaths with different depths.

Based on the respiratory waveform of the subject 2 displayed on the display device 15, the scan condition setting section 23 sets a scan duration and the scan start time according to the respiratory phase or level of the subject 2. The scan condition setting section 23 may automatically set the scan duration and the scan start time based on the respiratory waveform of the subject 2. Alternatively, the scan condition setting section 23 may be set by the operator by performing manual operation while observing the respiratory waveform of the subject 2 displayed on the display device 15. For the scan duration, a half scan or a full scan may be selected.

As is the case with the above-described first embodiment, two methods are available for the scan start timing for the subject 2. A first method specifies the respiratory phase of the subject 2 as an indication of the elapse of time. A second method specifies the respiratory level of the subject 2 as an indication of the depth of the breath. Any of a plurality of scan start timings can be set. The first method of specifying the respiratory phase of the subject 2 sets the scan start timing to be time t2 that is the predetermined delay time (d) after time t1 corresponding to the maximal expiration, based on the respiratory phase of the subject 2 captured by the respiration monitor 20 as shown in FIG. 3.

The method of specifying the respiratory level of the subject 2 as an indication of the depth of a breath sets the scan start timing to be time t10 corresponding to the inspiration level r1 that is a predetermined percentage, for example, 10% lower than the inspiration level rm indicating the maximal inspiration, based on the respiratory phase of the subject 2 captured by the respiration monitor 20 as shown in FIG. 4.

Figure 8:
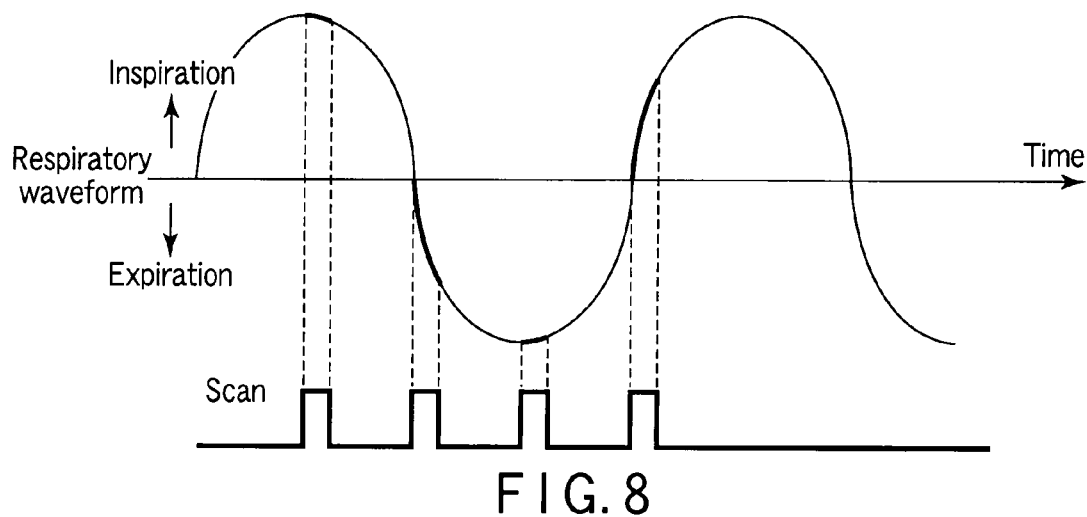
FIG. 8 is a diagram showing timings for allowing the apparatus to collect data when the respiratory cycle is long with respect to scan time.
Figure 9:
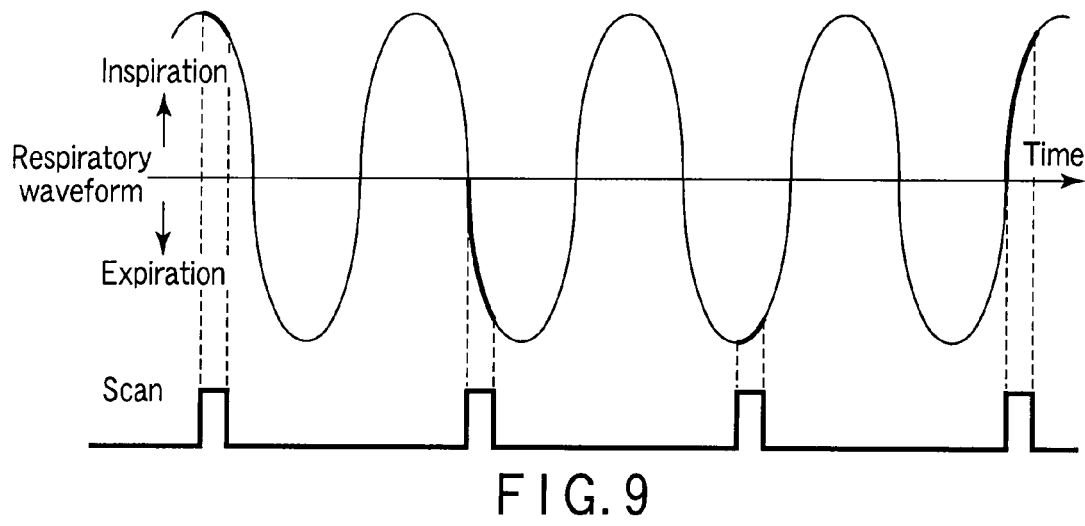
FIG. 9 is a diagram showing timings for allowing the apparatus to collect projection data when the respiratory cycle is short with respect to scan time.

FIGS. 8 and 9 show an example in which projection data is collected at four timings corresponding to peaks and valleys in the respiratory waveform corresponding to the maximal inspiration and maximum expiration of the subject 2 and the intermediate level between the maximal inspiration and the maximal expiration. FIG. 8 shows projection data collection timings provided when the respiratory cycle is long with respect to the scan duration. FIG. 8 indicates that for example, projection data can be collected at four respiratory phases during one cycle of respiratory waveform. FIG. 9 shows projection data collection timings provided when the respiratory cycle is short with respect to the scan duration. FIG. 9 indicates that projection data can be collected at intended phases over a plurality of respiratory cycles.

Figure 10:
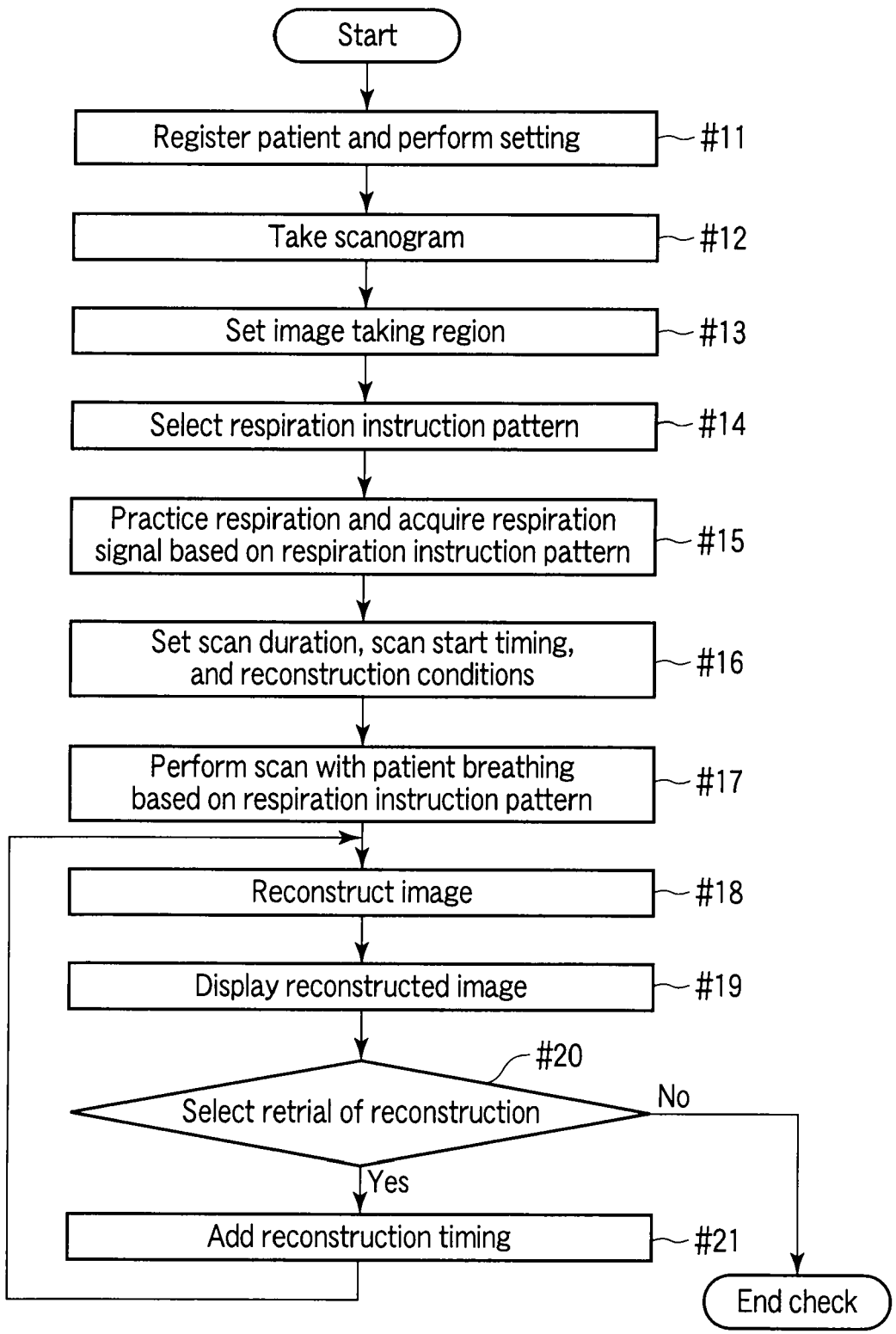
FIG. 10 is a flowchart of an operation of the apparatus during a single scan.

Now, the operation of the apparatus configured as described above will be described with reference to the operation flowchart shown in FIG. 10. FIG. 10 relates to an example of a single scan.

In step #1, the subject 2 such as a patient is registered, and the present apparatus is set. The subject 2 is laid on the bed in the gantry 1.

Then, in step #12, as described above, before acquiring a CT image of the subject 2, the present apparatus acquires a two-dimensional scan image of the subject 2. The scan image is acquired in order to determine, for example, the start position of the present scan and image capture conditions for acquiring the CT image.

The scan image is displayed on the display device 15 by the host controller 13. The operator observes the two-dimensional scan image of the subject 2 displayed on the display device 15. The operator, for example, manually operates the input device 16 to input an image capture range. The operator, for example, manually operates the input device 16 to select the respiration instruction pattern for the subject 2. In step #13, the host controller 13 sets the image capture range for the subject 2.

Then, in step #14, the host controller 13 sets the respiration instruction pattern for the subject 2.

Then, before the actual production scan, the apparatus has the subject 2 practice conscious breaths according to the voice instructions. In step #15, the respiration prompter 21 first outputs the voice message "Relax". Thus, the subject 2 maintains the normal breath (resting breath).

Then, the respiration prompter 21 outputs the voice message "Breathe in fully". Thus, the subject 2 takes a deep breath to enter the maximal inspiration state.

Then, the respiration prompter 21 outputs the voice message "Breathe out fully". Thus, the subject 2 breathes out fully to enter the maximal expiration state.

Then, the respiration prompter 21 outputs the voice message "Breathe in fully again". Thus, the subject 2 takes a deep breath again to enter the maximal inspiration state again.

Then, the respiration prompter 21 outputs the voice message "Relax". Thus, the subject 2 returns to the normal breath (resting breath).

Concurrently, in step #15, the respiration monitor 20 captures the motion of the subject 2 associated with respiration when the subject takes a breath in response to the voice instructions for respiration output by the respiration prompter 21. The respiration monitor 20 then outputs the resulting respiration monitoring signal. The respiration monitoring signal output by the respiration monitor 20 is stored in, for example, storage device 12. Concurrently, the respiration monitoring signal output by the respiration monitor 20 is transmitted to the display device 15, which displays a respiratory waveform, for example, as shown in FIG. 2.

Then, in step #16, based on the respiratory waveform of the subject 2 displayed on the display device 15, the scan condition setting section 23 sets the scan duration and scan start time of the production scan according to the respiratory phase or level of the subject 2. The scan condition setting section 23 may automatically set the scan duration and scan start time of the production scan based on the respiratory waveform of the subject 2. Alternatively, the scan condition setting section 23 may be set by the operator by performing manual operation while observing the respiratory waveform of the subject 2 displayed on the display device 15.

The scan control section 22 controls the timings for the production scan in response to the motion of the subject 2 associated with respiration, according to the start and end timings for the production scan set by the scan condition setting section 23. This timing control allows volume data on the subject 2 to be acquired. The reconstruction device 17 is set to reconstruct the volume data on the subject 2 to acquire a three-dimensional image of the desired respiratory phase.

Then, in step #17, the host computer 13 instructs the respiration prompter 21 to provide the subject 2 with the voice instructions of the same respiration instruction pattern as that for the practice of conscious breaths again. The host computer 13 also allows the respiration monitoring signal output by the respiration monitor 20 to be displayed on the display device 15.

During the production scan, the respiration prompter 21 first outputs the voice message "Relax". Thus, the subject 2 maintains the normal breath (resting breath).

Then, the respiration prompter 21 outputs the voice message "Breathe in fully". Thus, the subject 2 takes a deep breath to enter the maximal inspiration state.

Then, the respiration prompter 21 outputs the voice message "Breathe out fully". Thus, the subject 2 breathes out fully to enter the maximal expiration state.

Then, the respiration prompter 21 outputs the voice message "Breathe in fully again". Thus, the subject 2 takes a deep breath again to enter the maximal inspiration state again.

Then, the respiration prompter 21 outputs the voice message "Relax". Thus, the subject 2 returns to the normal breath (resting breath).

Concurrently, the respiration monitor 20 captures the motion of the subject 2 associated with respiration when the subject takes a breath in response to the voice instructions for respiration output by the respiration prompter 21. The respiration monitor 20 then outputs the resulting respiration monitoring signal. The respiration monitoring signal output by the respiration monitor 20 is stored in, for example, storage device 12. Concurrently, the respiration monitoring signal output by the respiration monitor 20 is transmitted to the display device 15, which displays a respiratory waveform, for example, as shown in FIG. 2.

In step #7, the host computer 13 outputs an instruction to perform the production scan, to the high-voltage generation device 6, the frame driving section 8, and the like via the data/control bus 14 so that the production scan is started according to the scan duration and scan start time of the production scan based on the respiratory phase or level of the subject 2 set by the scan condition setting section 23.

While the subject 2 is taking a conscious breath according to the voice instructions of the respiration instruction pattern, the X-ray tube 4 and the two-dimensional detection system 7 revolves continuously substantially around the subject 2. During a single scan, X-ray beams emitted by the X-ray tube 4 pass through the subject 2 and are detected by the two-dimensional detection system 7.

As described above, the DAS 9 converts an output through each channel of the two-dimensional detection system 7, into a voltage signal, amplifies the voltage signal, and further converts the amplified signal into a digital signal. The preprocessing device 11 corrects the inter-channel non-uniformity and the like of outputs from the DAS 9. The projection data preprocessed by the preprocessing device 11 is stored in the storage device 12.

For example, as shown in FIG. 8, if the respiratory cycle is long with respect to the scan duration, then during one cycle of respiratory phase, projection data is collected at, for example, four respiratory phases and stored in the storage device 12.

Furthermore, as shown in FIG. 9, if the respiratory cycle is short with respect to the scan duration, then projection data is collected at the intended phase over a plurality of respiratory phases and stored in the storage device 12.

Then, in step #18, for example, during the single scan, the reconstruction device 17 reconstructs CT images of a cross section of the subject 2, for example, 3D image data or 4D image data, from the projection data preprocessed by the preprocessing device 11. In this case, the reconstruction device 17 reconstructs projection data connected during the single scan set by the scan condition setting section 23.

Then, in step #19, the host computer 13 displays, on the display device 15, the three-dimensional image of the subject 2 at the desired respiratory phase acquired by the reconstruction device 17.

Then, in step #20, the host computer 13 determines whether or an additional scan is selected to be performed. If the host computer 13 determines that an additional scan is selected to be performed, the host computer 13 shifts to step #21 to add a scan timing and then returns to step #18. If no additional scan is selected to be performed, the host computer 13 ends the check.

Thus, according to the above-described second embodiment, the respiration prompter 21 outputs, for example, the voice messages "Relax", "Breathe in fully", "Breathe out fully", "Breathe in fully again", and "Relax", to the subject 2 to prompt the subject 2 to take conscious breaths with different depths. At this time, the X-ray tube 4 and the two-dimensional detection system 7 are continuously moved revolvingly substantially around the subject 2 to perform a single scan. Thus, projection data is collected.

Projection data can be collected not only while the subject 2 is breathing at rest but also when the subject 2 takes, for example, a breath ranging from the maximal expiration to the maximal inspiration. The reconstruction of the projection data, for example, enables a site that is hidden behind another site and cannot be observed at the resting respiration level to appear during the maximal expiration or the maximal inspiration. Thus, a CT image of the site can be observed.

Thus, diagnostic functional analysis or the like is enabled which is based on the motion of the subject 2 associated with a conscious deep breath, for example, the motion between the maximal expiration and the maximal inspiration. Consequently, even for a non-reproducible breath, projection data can be collected at any respiratory phase. Then, a CT image can be acquired by reconstructing the projection data.

For example, if the respiratory cycle is long with respect to the scan duration, then as shown in FIG. 8, during one cycle of respiratory phase, projection data is collected at, for example, four respiratory phases and stored in the storage device 12.

Furthermore, if the respiratory cycle is short with respect to the scan duration, then as shown in FIG. 9, projection data is collected at the intended phase over a plurality of respiratory phases and stored in the storage device 12.

Thus, projection data can be collected at a plurality of different respiratory phases during one cycle of respiratory phase of the subject 2. Selectively setting the scan duration and the scan start time allows projection data to be collected at any respiratory phase.

The present invention is not limited to the as-described embodiments. In practice, the components of the embodiments may be varied without departing from the spirit of the present invention. Furthermore, various inventions can be formed by appropriately combining a plurality of the components disclosed above in the embodiments. For example, some of the components disclosed in the embodiments may be omitted. Moreover, components from the different embodiments may be appropriately combined together.

Figure 11:
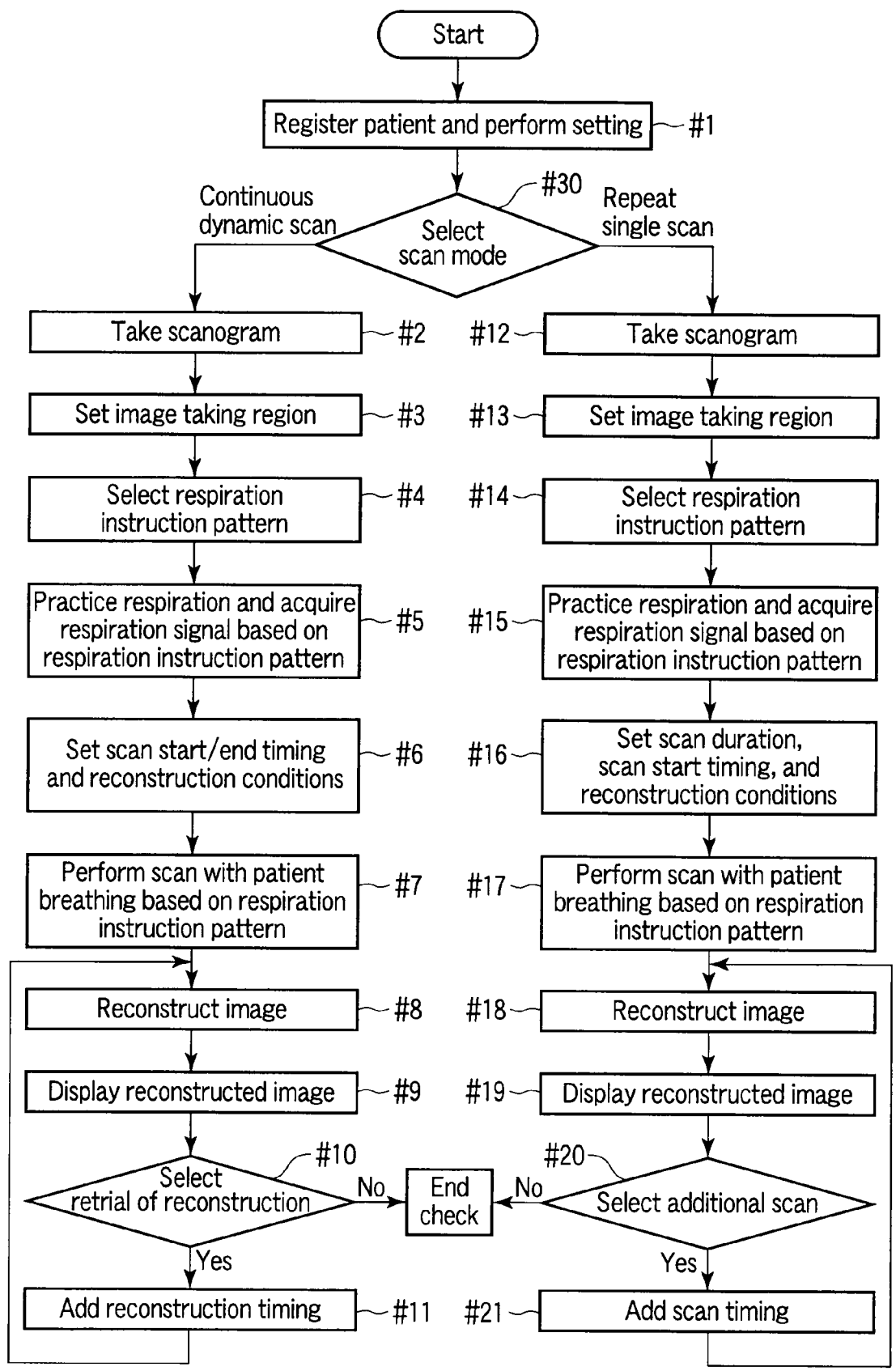
FIG. 11 is a flowchart of an operation of the apparatus which enables the continuous dynamic scan or the single scan to be selected.

The first embodiment has been described in conjunction with the application to the continuous dynamic scan. The second embodiment has been described in conjunction with the application to the single scan. However, the present invention is not limited to this aspect. In the present apparatus, the host controller 13 may provide the determination function of selecting one of the continuous dynamic scan and the single scan. For example, as shown in FIG. 11, in step #30, the host controller 13 selects the scan mode, that is, either the continuous dynamic scan or the single scan.

To allow the continuous dynamic scan or the single scan to be set, for example, a scan mode switch is provided such that, for example, the operator manually operates and sets the switch to the continuous dynamic scan or the single scan. The host controller 13 determines whether the scan mode switch is set to the continuous dynamic scan or the single scan. In this case, an operation flowchart for the continuous dynamic scan is the same as that shown in FIG. 7. An operation flowchart for the single scan is the same as that shown in FIG. 10.

The present apparatus is applicable not only to the cone-beam X-ray CT apparatus emitting cone-beam X-rays but also to a multi-slice X-ray CT. The multi-slice X-ray CT includes an X-ray source emitting conical X-ray beams and a two-dimensional detector with a plurality of detection elements arranged on a cylindrical surface so that N fan beam detection rows each of a plurality of (M) fan beams are stacked in the direction of the Z-axis.

The voice instructions for respiration are not limited to "Relax", "Breathe in fully", "Breathe out fully", "Breathe in fully again", and "Relax". The voice instructions may include another one, for example, "Hold your breath". The voice instructions for respiration may indicate the depth of the breath; for example, "Take a small breath" and "Breathe out a little" are possible.

Figure 12:
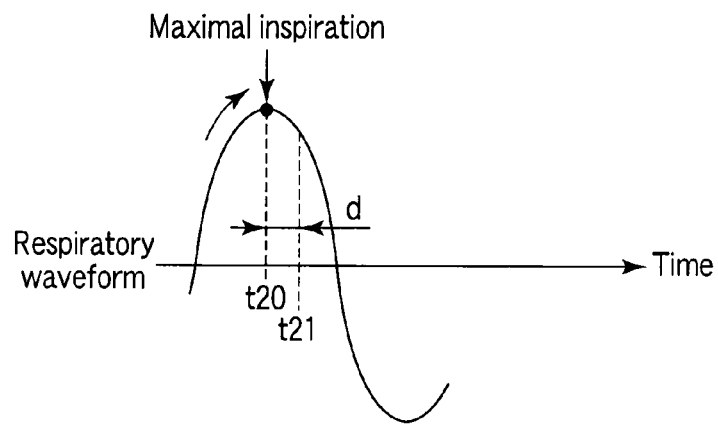
FIG. 12 is a diagram showing a variation of a timing for allowing the apparatus to start a production scan.

As shown in FIG. 12, the timing for starting the production scan is set by detecting variation in the respiratory waveform of the subject 2 captured by the respiration monitor 20, and determining time t20 to correspond to the maximum inspiration; the scan is started at time t21 that is the predetermined delay time (d) after time t20 when the respiratory waveform of the subject 2 changes, for example, from upward variation to downward variation.

Alternatively, the timing for starting the production scan may be set by detecting variation in the respiratory waveform of the subject 2 captured by the respiration monitor 20, and determining the time when the respiratory waveform of the subject 2 changes, for example, from downward variation to upward variation to correspond to the maximum expiration; the scan may be started the predetermined delay time (d) after the above-described time.

What is claimed is:

1. An X-ray CT apparatus comprising:
   an X-ray generation section configured to irradiate a subject with a cone-beam X-ray emitted by an X-ray source;
   a two-dimensional detector formed as a two-dimensional plane to detect the X-ray beam having passed through the subject;
   a data acquisition section configured to collect data from the two-dimensional detector to acquire volume data on the subject;
   a respiration prompter configured to sequentially vocalize a plurality of breathing instructions to the subject to prompt the subject to breathe with different respiration depths before and during irradiation;
   a respiration monitor configured to capture subject motion associated with respirations of different depths prompted by the breathing instructions sequentially vocalized by the respiration prompter;
   a scan control section configured to control timing for irradiation of the subject with the X-ray beam according to the subject's motion associated with different respiration depths and captured by the respiration monitor;
   a display section displaying the subject's motion associated with respiration and captured by the respiration monitor, as a respiratory waveform; and
   a scan condition setting section setting the start and end of the irradiation according to the subject's respiratory phase or level based on the subject's respiratory waveform displayed on the display section,
   wherein a period of irradiation of the subject includes at least part of an inspiration and part of an exhalation of a same respiratory cycle,
   the scan control section controls a timing for each of start and end of the irradiation of the X-ray beam according to the subject's respiratory phase or level captured by the respiration monitor,
   the scan control section starts the irradiation of the X-ray beam at least a predetermined time after a time corresponding to a maximal inspiration, based on the subject's respiratory phase captured by the respiration monitor, and
   the scan control section controls the timing for each of the start and end of the irradiation according to the subject's respiratory phase or level set by the scan condition control section.

2. The X-ray CT apparatus according to claim 1, wherein the respiration prompter vocalizes the breathing instructions sequentially to prompt the subject to breathe restfully and deeply as the different respiration depths.

3. The X-ray CT apparatus according to claim 1, wherein the respiration prompter vocalizes the breathing instructions including at least sequentially instructing the subject to breathe easily, to breath in fully, and to breathe out fully.

4. The X-ray CT apparatus according to claim 1, wherein the prompter vocalizes the breathing instructions sequentially to prompt the subject to take breaths of different respiration depths before the irradiation with the X-ray beam and during the irradiation with the X-ray beam.

5. The X-ray CT apparatus according to claim 1, wherein the scan control section finishes the irradiation of the X-ray beam at least a half cycle or one cycle of the respiratory phase after the start of the irradiation of the X-ray beam.

6. An X-ray CT apparatus comprising:
   an X-ray generation section configured to irradiate a subject with a cone-beam X-ray emitted by an X-ray source;
   a two-dimensional detector formed as a two-dimensional plane to detect the X-ray beam having passed through the subject;
   a data acquisition section configured to collect data from the two-dimensional detector to acquire volume data on the subject;
   a respiration prompter configured to sequentially vocalize a plurality of breathing instructions to the subject to prompt the subject to breathe with different respiration depths before and during irradiation;
   a respiration monitor configured to capture subject motion associated with respirations of different depths prompted by the breathing instructions sequentially vocalized by the respiration prompter; and
   a scan control section configured to control timing for irradiation of the subject with the X-ray beam according to the subject's motion associated with different respiration depths and captured by the respiration monitor,
   wherein a period of irradiation of the subject includes at least part of an inspiration and part of an exhalation of a same respiratory cycle,
   the scan control section controls a timing for each of start and end of the irradiation of the X-ray beam according to the subject's respiratory phase or level captured by the respiration monitor, and
   if the irradiation of the subject repeats a single scan, the scan control section performs the single scan according to the subject's respiratory phase or level captured by the respiration monitor, and the data acquisition section collects data from the two-dimensional detector to acquire the volume data on the subject at a desired respiratory phase.

7. A scan control method for an X-ray CT apparatus, the method comprising:

sequentially vocalizing, from a respiration prompter, a plurality of breathing instructions to a subject to prompt the subject to breathe with different respiration depths before and during irradiation;

capturing, at a respiration monitor, subject motion associated with different respiration depths prompted by the breathing instructions sequentially vocalized by the respiration prompter;

controlling, in a scan control section, a timing when the subject is irradiated with a cone-beam X-ray emitted by an X-ray source, according to the subject motion associated with different respiration depths and captured by the respiration monitor;

detecting, in a two-dimensional detector formed as a two-dimensional plane, the X-ray beam having passed through the subject;

collecting, in a data acquisition section, data from the two-dimensional detector to acquire volume data on the subject;

displaying the captured motion of the subject associated with respiration, as a respiratory waveform; and setting the start and end of the irradiation according to the subject's respiratory phase or level based on the displayed respiratory waveform of the subject, wherein a period of irradiation of the subject includes at least part of an inspiration and part of an exhalation of a same respiratory cycle, a timing for each of start and end of the irradiation of the X-ray beam is controlled according to the captured respiratory phase or level of the subject, the scan is started at least a predetermined time after a time corresponding to a maximal inspiration, based on the captured respiratory phase of the subject, and the timing for each of the start and end of the irradiation is controlled according to the set respiratory phase or level of the subject.

8. The scan control method for the X-ray CT apparatus according to claim 7, wherein the prompting to take breaths comprises vocalizing the breathing instructions sequentially to prompt the subject to breathe restfully and deeply as the different respiration depths.

9. The scan control method for the X-ray CT apparatus according to claim 7, wherein the prompting to take breaths comprises vocalizing the breathing instructions including at least sequentially instructing the subject to breathe easily, to breathe in fully, and to breathe out fully.

10. The scan control method for the X-ray CT apparatus according to claim 7, wherein the prompting to take breaths vocalizes the breathing instructions sequentially to prompt the subject to take breaths of different respiration depths before the irradiation with the X-ray beam and during the irradiation with the X-ray beam.

11. The scan control method for the X-ray CT apparatus according to claim 7, wherein the irradiation of the X-ray beam is finished at least a half cycle or one cycle of the respiratory phase after the start of the irradiation of the X-ray beam.

12. A scan control method for an X-ray CT apparatus, the method comprising:

sequentially vocalizing, from a respiration prompter, a plurality of breathing instructions to a subject to prompt the subject to breathe with different respiration depths before and during irradiation;

capturing, at a respiration monitor, subject motion associated with different respiration depths prompted by the breathing instructions sequentially vocalized by the respiration prompter;

controlling, in a scan control section, a timing when the subject is irradiated with a cone-beam X-ray emitted by an X-ray source, according to the subject motion associated with different respiration depths and captured by the respiration monitor;

detecting, in a two-dimensional detector formed as a two-dimensional plane, the X-ray beam having passed through the subject; and collecting, in a data acquisition section, data from the two-dimensional detector to acquire volume data on the subject, wherein a period of irradiation of the subject includes at least part of an inspiration and part of an exhalation of a same respiratory cycle, the scan is started at least a predetermined time after a time corresponding to a maximal inspiration, based on the captured respiratory phase of the subject, and if the scan of the subject comprises repeating a single scan, the single scan is performed according to the captured respiratory phase or level of the subject, and data is collected from the two-dimensional detector to acquire the volume data on the subject at a desired respiratory phase.

* * * * *